United States Patent [19]

Tepic

[11] Patent Number: 5,591,448
[45] Date of Patent: Jan. 7, 1997

[54] ANTI-VIRAL THERAPEUTIC COMPOSITION

[76] Inventor: Slobodan Tepic, AO-Forschungsinstitit AISF Research Institute Clavadelerstrasse, CH-7270 Davos, Switzerland

[21] Appl. No.: 345,465

[22] Filed: Nov. 21, 1994

[51] Int. Cl.$^6$ ................................................ A61K 9/127
[52] U.S. Cl. ...................... 424/450; 428/402.2; 436/829
[58] Field of Search .................. 424/450; 428/402.2; 436/829

[56] References Cited

U.S. PATENT DOCUMENTS

| | | | |
|---|---|---|---|
| 4,501,728 | 2/1985 | Geho | 424/38 |
| 4,605,630 | 8/1986 | Kung | 436/511 |
| 4,652,257 | 3/1987 | Chang | 604/52 |

FOREIGN PATENT DOCUMENTS

| | | |
|---|---|---|
| 0176429 | 9/1985 | European Pat. Off. . |
| 0298280 | 6/1988 | European Pat. Off. . |

*Primary Examiner*—Gollamudi S. Kishore

[57] ABSTRACT

The novel therapeutic composition of matter is useful against the class of viruses possessing an outer lipid envelope. It consists of the association of a liposome and a viral receptor protein whereby the larger, receptor-carrying liposome is coated by a number of small liposomes reducing antigenicity of the complex. The size of viral particles allows them free access to the receptors. Receptor mediated fusion of the viral envelope and the larger liposome's membrane engulfs the viral core.

7 Claims, 9 Drawing Sheets

ANTI-VIRAL THERAPEUTIC COMPOSITION

CROSS-REFERENCE TO RELATED APPLICATIONS

This application is a continuation-in-part of U.S. patent application Ser. No. 08/155,572, filed on Nov. 22, 1993, now abandoned.

BACKGROUND OF THE INVENTION

The present invention relates to a therapeutic composition of matter for use against the class of viruses possessing an outer lipid envelope.

Aquired immune deficiency syndrome, or AIDS, is a most threatening pandemic of modern times. The cause of the AIDS has been identified as a human retrovirus, most recently referred to as HIV (Human Immunodeficiency Virus). The virus enters into, resides and replicates within CD4 lymphocytes. Replication of the virus is possible only within an activated lymphocyte. Other cells may also be infected, in particular macrophages, but in contrast to the CD4 lymphocyte, these will not be easily killed by the virus. The population of CD4 lymphocytes is reduced and disabled by the replicating virus, the immune system is compromised, and the patient ultimately dies of some other infection or tumor.

The genetic material of HIV is RNA, which is, together with reverse transcriptase enzyme, encapsulated in the core of the virus, the core consisting of two proteins. In the process of budding out from the host cell the core of the virus becomes enveloped in a lipid bi-layer from the outer membrane of the host. The envelope also contains viral glycoproteins—the only functional component of the virus-specific makeup when it is outside a host cell. These envelope glycoproteins (referred to as gp120) are the only source of antigen of an enveloped virus. Variability in their structure, even within an individual patient, makes the development of a vaccine a difficult task. Most efforts to curb the spread of AIDS and to prevent it from taking its toll from an already infected population are currently directed towards development of an efficient therapy.

None of the clinically tested therapies to date are satisfactory including AZT, Interferons, Interleukins, and Monoclonal antibodies to CD4 or to HIV.

SUMMARY OF THE INVENTION

The invention as claimed is intended to remedy these drawbacks and to provide an efficient therapeutic composition for treating viral diseases, in particular AIDS, and any other infection having an agent's mechanism similar to that of HIV.

The therapeutic composition of the present invention consist of modified liposomes that act like "decoys" by causing the virus to interact with the liposome, or decoy, receptors. The virus cores are then "engulfed" by the liposome, while each virus leaves its envelope behind in the decoy membrane.

Proteins in general, and even more those that act as receptors on liposomes, are strongly antigenic and would provoke reaction of the immune system clearing them out from circulation very quickly. CD4 interacts with MHC II found on many cells and its water soluble form has now been shown to be toxic when administered intravenously. Rationale for its use in that way was to have CD4 bind to gp120 on HIV and neutralize it by preventing its interaction with CD4-carrying cells.

The problem of unwanted interactions of CD4 with host cells is solved by this invention—the CD4-carrying liposomes are coated by a number of smaller liposomes bearing no proteins other than a link protein used to attach the small liposomes to large ones. The size and number of small liposomes are chosen so that gaps between them allow HIV particles to get through these gaps and reach the surface of the large liposome where interaction with CD4 leads to fusion and delivery of the viral core into the large liposome. Vital particles are about 0.1 micrometers in diameter—smaller than any cellular features likely to develop in circulation. The principle of size exclusion should thus allow for selective action of the CD4 carrying liposomes against HIV.

The present invention solves the problem of how to design non-antigenic "decoys" for the virus to enter, whereby the virus is stripped of its envelope. A number of steps may be taken following entrapment of the virus, but in no way will it be allowed to return to the state in which it exists following budding from a host, e.g. a CD4 lymphocyte.

It is well established that HIV primarily enters cells with the CD4 protein in their outer (plasma) membranes. CD4 is abundant in the plasma membrane of the CD4 lymphocyte, but is also found in monocytes, macrophages and perhaps, in small numbers, in many other cells. It is probably through the interaction of the viral envelope glycoprotein gp120 and the CD4 protein that the cell's membrane opens, fusing with the vital envelope, while the viral core enters the cell. Action of an intracellular enzyme on the inner part of the CD4 membrane-anchoring segment (its phosporylation by protein kinase C) appears to be needed for the fusion of the membranes—if the action of this enzyme is inhibited, HIV particles attach to CD4 but fusion of the membranes does not follow (FIELDS, et al., Nature, Vol. 333, May 1988).

This process is imitated in the method according to the invention by an "artificial cell"—a liposome with a CD4 protein, or a CD4 protein fragment, or an equivalent thereof integrated into the liposome's membrane, whereby the CD4 carrying liposome is coated by a number of smaller liposomes carrying no antigens, making the complex very neutral. CD4-carrying liposome may also be loaded (its interior) by other components of the fusion-facilitating system, such as protein kinase C, as well as by antiviral substances.

BRIEF DESCRIPTION OF THE DRAWINGS

The various features of novelty which characterize the invention are pointed out with particularity in the claims annexed to and forming part of this disclosure. For better understanding of the invention, its operating advantages and specific objects attained by its use, reference should be had to the accompanying drawings and descriptive matter in which are illustrated and described preferred embodiments of the invention.

In the drawings.

DESCRIPTION OF THE PREFERRED EMBODIMENTS

Figure 1:
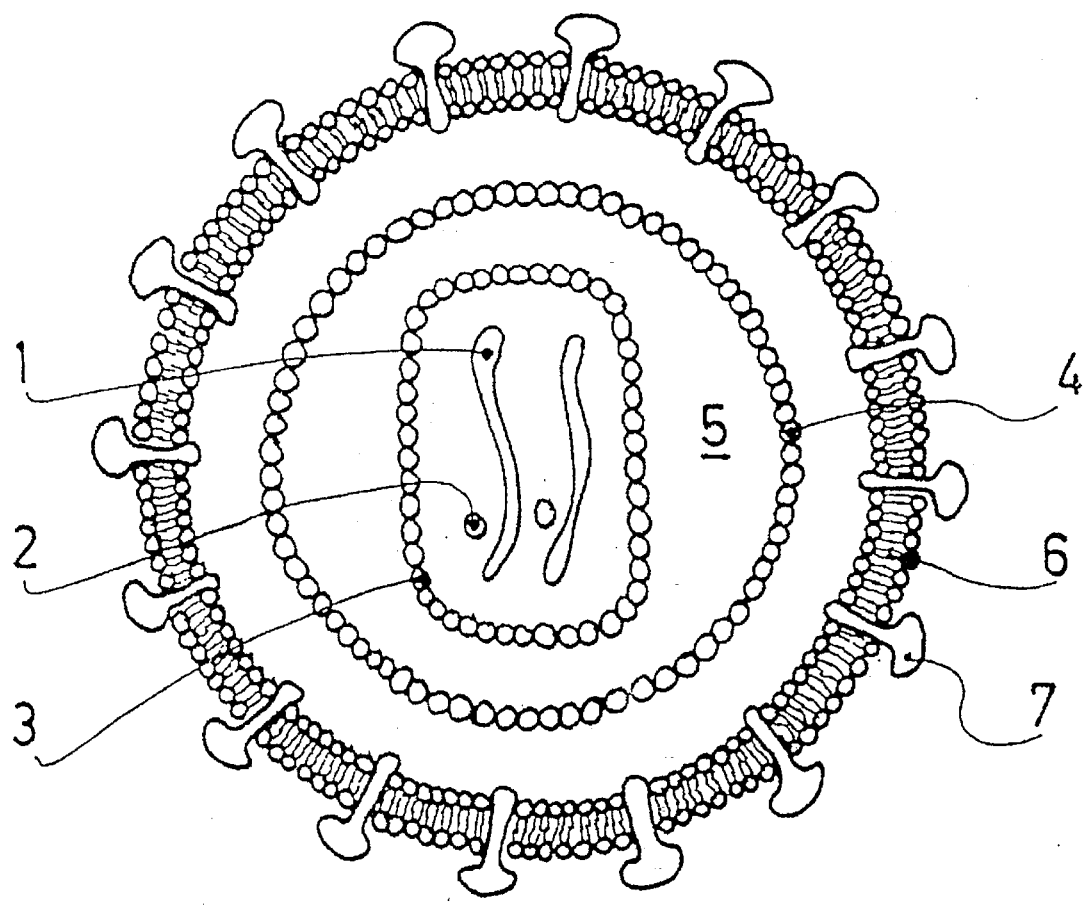
FIG. 1 is a schematic representation of the internal structure of a Human Immunodeficiency Virus (HIV)
Figure 2:
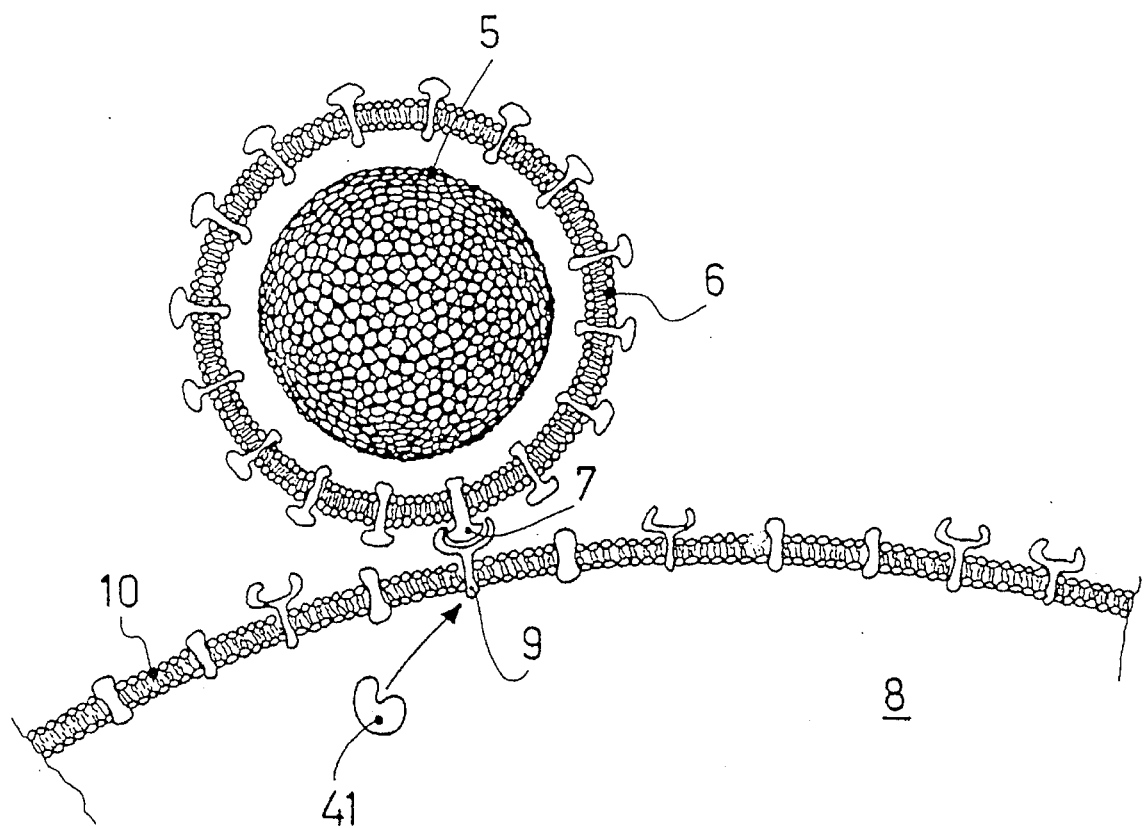
FIG. 2 is a schematic representation of a virus at the moment of attachment to the host cell.
Figure 3:
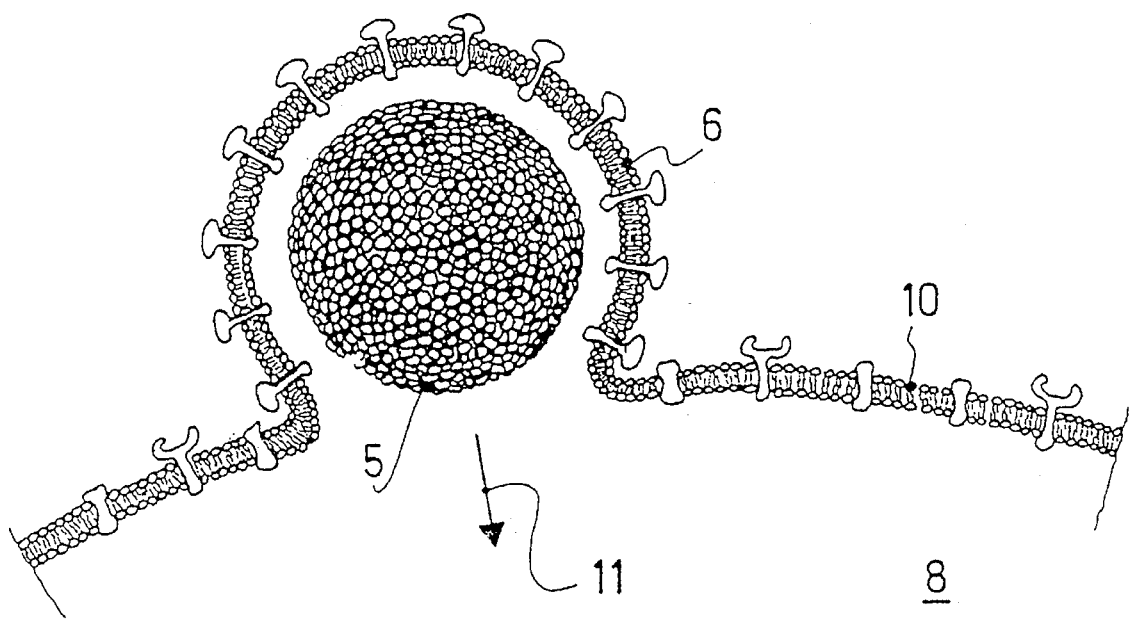
FIG. 3 is a schematic representation of the virus of FIG. 2 whose lipid layer has fused with that of the host cell.
Figure 4:
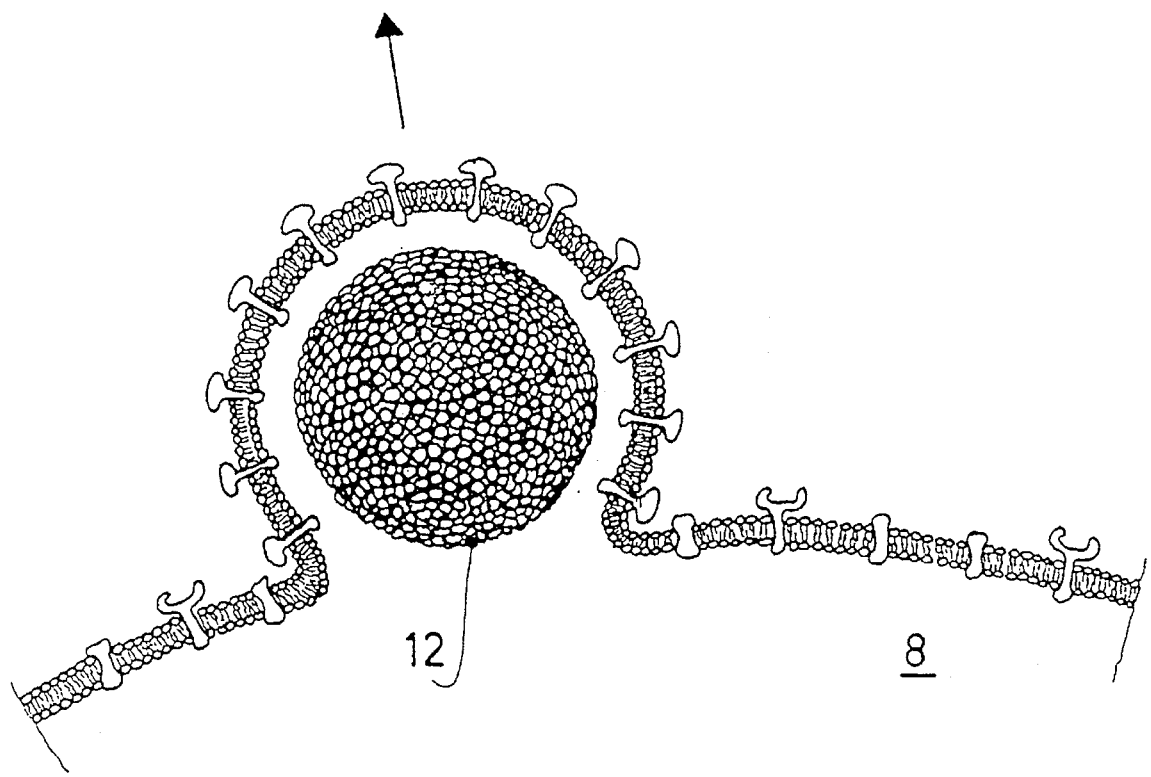
FIG. 4 is a schematic representation of a new viral core budding out of the host cell of FIG. 2.
Figures 5A, 5B:
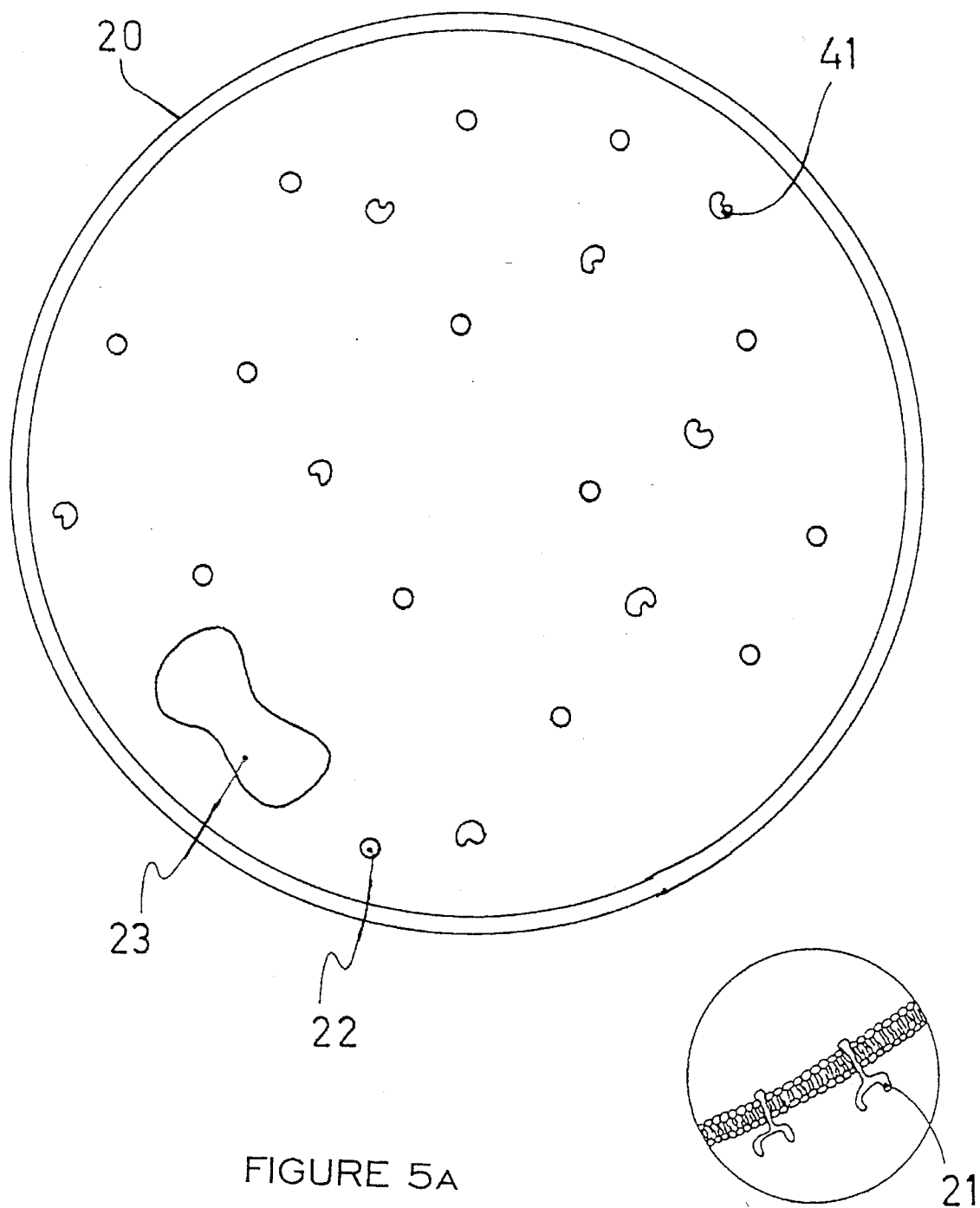
FIGS. 5a and 5b show a decoy according to the invention consisting of a liposome carrying CD4 proteins with FIG. 5b showing a detail view of the CD4 protein incorporated into the lipid bilayer.
Figure 6:
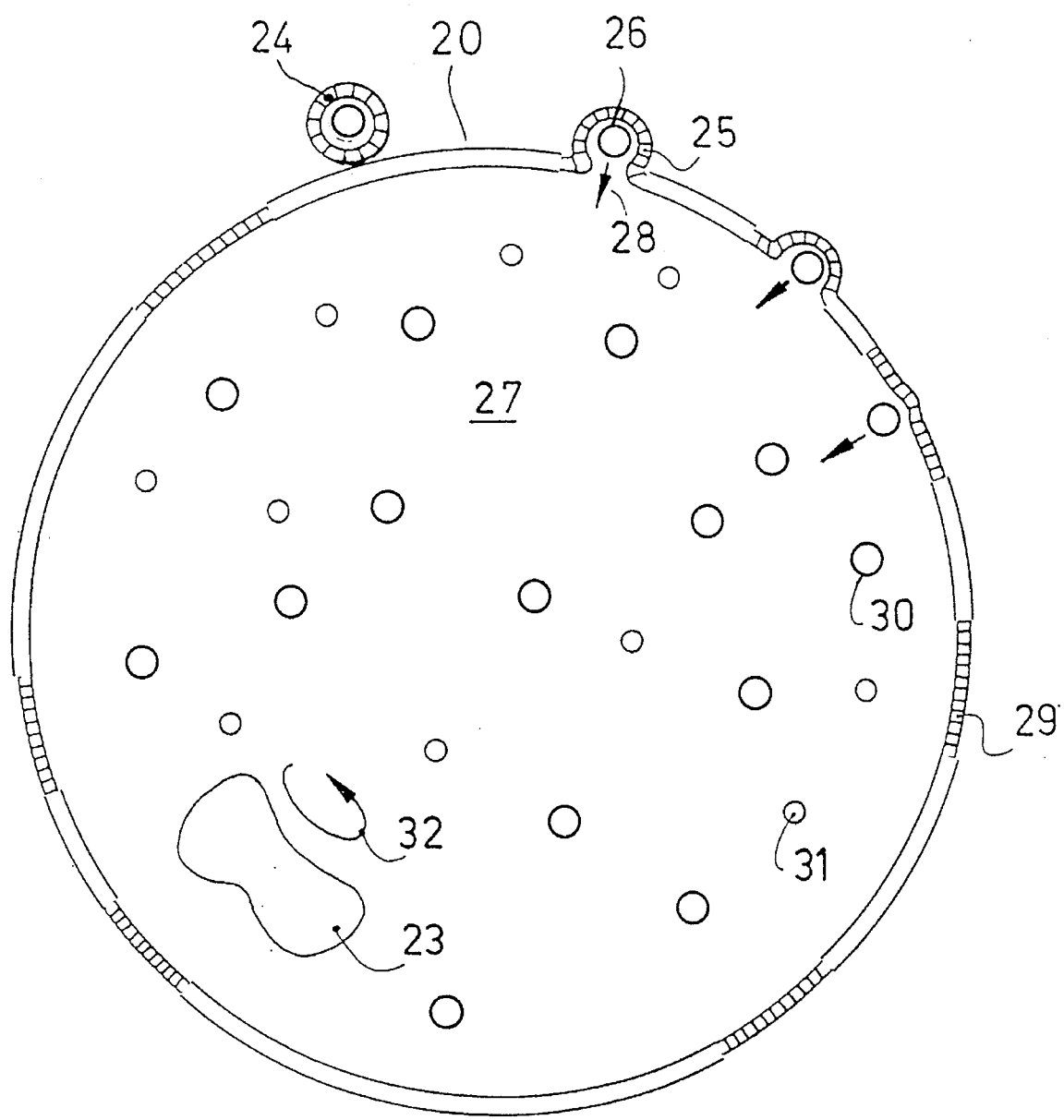
FIG. 6 shows viruses in different stages of entry into the decoy of FIG. 5.

The present invention is directed to therapeutic composition of matter for use against the class of viruses possessing an outer lipid envelope, such as the Human Immunodeficiency Virus. The novel composition comprises a receptor protein (CD4) anchored in a liposome's membrane so that CD4 is capable of interacting with the envelope protein (gp120) of the virus. This allows the liposome to engulf the viral core. To prevent interactions of CD4 with host cells, particularly all those that carry MHC II, the CD4-carrying liposome is covered by a number of small liposomes, making the complex virtually non-antigenic (not more than the phospholipid bilayer itself).

Liposome preparation, as well as incorporation of membrane proteins into liposomes, is a known, well developed art—much of the relevant technology is described in detail in "Liposome Technology", Vols. I to III edited by Gregory Gregoriadis, published by CRC Press Inc., Boca Raton, Fla. (1984), which is herein incorporated by reference.

The preparation of the therapeutic composition according to the present invention is based on the unique behavior of phospholipids. Phospholipids, the major structural components of cell membranes, are molecules unique in their amphipatic design. Composed of hydrophobic (water-insoluble) tail and a hydrophilic (water-soluble) head, phospholipids, when combined with water, undergo a spontaneous reorganization that results in the formation of a self-contained, fluid filled vesicle called a liposome.

A cross-section of the liposome structure show a phospholipid bilayer in which the hydrophobic tails of each layer align themselves, to the exclusion of water, towards the membrane's interior. The hydrophilic head groups, in turn, point outward in opposite directions, seeking to bind the water that is present both in and around the liposome. As the liposome forms, any water-soluble molecules introduced into the phospholipid solution become assimilated into the vesicle's water-filled interior, whereas any lipid-soluble molecules added to the solution become incorporated into the liposome's phospholipid bilayer. It is this unique behavior of phospholipids in the aqueous state that enables one to load drugs into liposomes for use as a vehicle in drug-delivery.

Specific concerns of production of liposomes, such as purity, encapsulation efficiency, uniformity, stability, costs, etc. are not unique to this invention. While the choice of one or more of the existing methods of making liposome-based compositions depends on these production considerations, no unique method of making is necessary to realize the invention.

The CD4 protein may be purified from the natural cultured cells with the aid of the anti-CD4 antibody, or it may be synthetic. Methods for obtaining CD4 protein from a culture of CD4 lymphocytes are described by C. TERHORST et al. in SCIENCE (1980), 2.09, 520–521 and by E. L. REINHERZ et al. in PROC.NATL.ACAD.SCI.USA (1979), Vol. 76, 4061–4065, both of which are hereby incorporated by reference. In January of 1988 four groups (FISHER et al., HUSSEY, et al., DEEN, et al., TRAUNECKER, et al., Nature, Vol 331) have reported on production of CD4 by recombinant DNA techniques—they are herein incorporated by reference.

Methods for anchoring cellular membrane receptors in general, and thus of the CD4 protein as well, in the liposome's membrane are described on "Liposome Technology" Vol. I to III edited by Gregory Gregoriadis, published by CRC Press Inc., Boca Raton, Fla. (1984), which is hereby incorporated by reference. The CD4 protein used in the present invention is a membrane protein. The CD4 protein would be used in the manner of membrane proteins listed in Table I of Chapter 10 of "Liposome Technology".

The CD4 protein is incorporated into the bilayer of the liposome membrane. To start, unilamellar liposomes are formed by any known method. One way of obtaining the proper preparations is to pass a solution of detergent, phospholipids, and CD4 proteins through a gel chromatography column to remove the detergent. This method of liposome preparation yields unilamellar liposomes with most of the CD4 proteins oriented in a right-side-out direction. The method can only be used with detergents that have a high critical micelle concentration and a correspondingly low molecular weight of the micelles. Examples of these types of detergents are the bile sates sodium cholate, sodium deoxycholate, and the nonionic detergent beta-D-octylglucoside. These detergents can easily be removed from a phospholipid mixture by gel chromatography on SEPHADEX TM G 25 or G 50.

The critical micelle concentration of the detergents and the molecular weight of the micelles are affected by the ionic strength and the pH of the buffer. A higher ionic strength decreases the critical micelle concentration and increases the molecular weight of the micelles. For example, sodium deoxycholate can be separated from the phospholipids by a G 25 column using an elution buffer with low ionic strength. However, the same separation must be made on a G 50 column if a phosphate buffer pH 7.5 is used.

It is known already to use liposomes containing an antiviral agent with the anti-CD4 antibodies in the membrane. These liposomes will be attracted to the CD4 carrying cells and release the antiviral agent.

If, however, according to the invention, the CD4 protein itself (instead of the anti-CD4 antibody) or a part of it responsible for the interaction with the HIV, or an equivalent, is incorporated in the membrane, the liposome will become a "decoy" and collect the virus. On entry the virus leaves its envelope behind in the decoy membrane. Virus-collecting efficacy of such decoy liposomes depends on the number of CD4 molecules they carry. Size of the decoy plays a certain role, but is not a limiting factor. Surface-to-volume ratio of the virus is higher than that of the decoy so the viral membrane incorporated into liposomes will make for the volume of enclosed core. With increasing numbers of engulfed virus, the membrane will tend to slack out. Liposome diameter is preferably in the range of one to ten microns. In vivo liposomes compete for the virus against the natural CD4-carrying cells. Low antigenicity of decoys coated by small liposomes allows for manifold increase of CD4 targets and thus reduces the infection rate of natural CD4-carrying cells.

A CD4 protein fragment is a portion of the CD4 protein that is sufficient for the HIV to "think" that, i.e., to react as if, the liposome is a CD4 lymphocyte cell. A CD4 protein equivalent mimics the CD4 protein, or a portion of the CD4 protein, so that the human immunodeficiency virus (HIV) is fooled into "thinking" that the liposome with the CD4 protein equivalent is a CD4 lymphocyte cell.

The CD4 protein employed in the present invention is anchored in the liposome membrane. The CD4 protein is either an artificial or natural receptor for the viral envelope protein, but is not the viral envelope protein itself. The protein (21, FIG. 5*a*) which is anchored to the liposome's membrane interacts with the envelope protein of the virus (see protein 7, FIG. 1). This allows the liposome to engulf the core (26 and 30, FIG. 6) of the virus.

Once the virus has been collected by liposomes, a number of steps may be taken to render it harmless:

(1) No further action. Supposing that any liposome will eventually be degraded in vivo, the viral cores will find themselves exposed to either blood or lymph. The cores will not find a way to envelop themselves either in the process of liposome degradation, or later. Without its envelope, the viral core loses most or its infectivity. It may be destroyed, or it may provoke a better-targeted immune response. Thus the simplest therapeutic procedure is based on stripping the virus of its envelope by CD4 marked liposome decoys, which then degrade and dump the viral cores.

(2) Break up decoys by external action. Liposomes can be made to contain a magnetizable particle. Once the virus is collected, these particles can be magnetized by a strong magnetic field and then set in rotation by a rotating magnetic field. This breaks the liposome membrane and spills the contents—bare viral cores. To avoid aggregation, magnetic particles can be immediately demagnetized by a high frequency alternating field.

(3) Decoys may be loaded with antiviral agents. The fact that the virus is stripped of its envelope on entry into liposome helps—an enzyme that breaks the core protein(s) suffices. Other antiviral agents can be used as well e.g. heteropolyanionic compositions according to French Patent 73.27.536/2.245.474 (hereby incorporated by reference), ribaverine or lincomycine (marketed under the trademark LYNCOCYNE) or clindamycine as described in "Molecular Basis of Antibiotic Action" by Gale et al. (1972), 678, 2d. edition, by Wiley and Sons, and hereby incorporated by reference. Either natural of forced destruction of liposomes completes the process.

(4) Decoys may be marked with a second, stable antigen (that even the depressed immune system will react to). Basically as above, but the liposome destruction is sought via immune response.

(5) Activate CD4 lymphocytes to bring out dormant virus. Activation may be brought about from outside, e.g. by injection of appropriate lymphokines, or by step (4).

On one side liposomes are competing for the virus and provoking the immune response against themselves. Activation pushes infected CD4 lymphocytes to express the virus, dying in the process and spilling out a new generation of virus which is picked up by the decoys. This may offer a chance for thorough elimination of the virus from its major host—CD4 lymphocyte.

FIG. 1 shows the structure of the Human Immunodeficiency Virus (HIV) as currently understood. The genetic material 1 is in the form of RNA. It is accompanied by reverse transcriptase enzyme 2, which, upon release within the host cell, transcribes ribonucleic acid (RNA) to deoxyribonucleic acid (DNA) to be incorporated into the host's own DNA. Two core proteins, 3 and 4, encapsulate the RNA and the enzyme in the viral core 5. The outer envelope of the virus is a lipid bi-layer 6. Viral envelope glycoproteins 7 are embedded in the lipid bi-layer 6. The diameter of the virus is about one tenth of a micrometer.

FIG. 2 shows a virus at the moment of attachment to the host cell 8. An envelope glycoprotein 7 (gp120) binds to a cell membrane protein 9, which to the best current knowledge is the CD4 protein. Interaction between proteins 7 and 9 pulls the two lipid layers 6 and 10 together so they can fuse and open a way for the viral core 5 to enter the cell as shown by arrow 11 on FIG. 3. It appears now that following binding of the proteins 7 and 9, a further step of phosphorylation of receptor 9 (CD4) by an enzyme protein kinase C, contained within the cell is necessary for fusion to take place. Protein kinase C is shown as 41 on FIG. 2, its action on the anchor of 9 marked by an arrow. Host cell enzymes proceed to cut the core proteins, releasing the RNA and reverse transcriptase.

FIG. 4 shows a new viral core 12 budding out from the host cell 8. In the case of the CD4 lymphocyte, the cell 8 dies at this time with a burst of new viruses spreading out into circulation.

FIG. 5*a* shows a decoy consisting of a liposome carrying CD4 proteins, or an equivalent. Liposome membrane 20 is a lipid bi-layer. It resembles the natural cell membrane. Decoys are not expected to leave circulation and the preferred type of the liposome is a large unilamellar vesicle (LUV) with a diameter between one and ten microns. As shown in FIG. 5*b*, which shows a detail view of the decoy membrane 20, the CD4 protein 21 is incorporated in the decoy membrane 20. It may be complete or only part of it responsible for the entry of the HIV into natural cells. The liposome may additionally be loaded with an antiviral agent 22. Only the viral core enters the liposome and an enzyme capable of disrupting the vital core proteins will suffice. The liposome is also loaded by protein kinase C, 41.

The liposome may further contain a magnetizable substance, or particle 23. This allows for external, directed destruction of decoys.

For ease in understanding the mechanism of the liposomes of this invention, reference is made to FIG. 6 where it is shown that the envelope (lipid bilayer and envelope protein—gp120) of the virus is inserted into the liposome membrane, but the core of the virus is trapped in the interior of the liposome. This is much like the way host/cells are invaded as shown in FIGS. 2–4, but the liposomes of this invention act as a "decoy", saving the host cell.

FIG. 6 shows virus in different stages of entry into the decoy. One virus 24 has approached the membrane 20; the envelope of another one 25 has fused with the decoy's membrane 20, and its core 26 is entering the liposome's inner space 27 as shown by arrow 28. Membranes 29 of the viral cores 30 already within the liposome are integrated into the liposome membrane 20. An enzyme as a possible antiviral agent is shown with empty circles 31; protein kinase C is maked as 41.

Magnetizable particle 23 may be magnetized and set in rotation by an external magnetic field, as shown by arrow 32. Drag of the surrounding fluid will eventually cause the decoy to rupture, dumping the content into circulation. Particles 23 can be immediately demagnetized to avoid aggregation.

Figure 7:
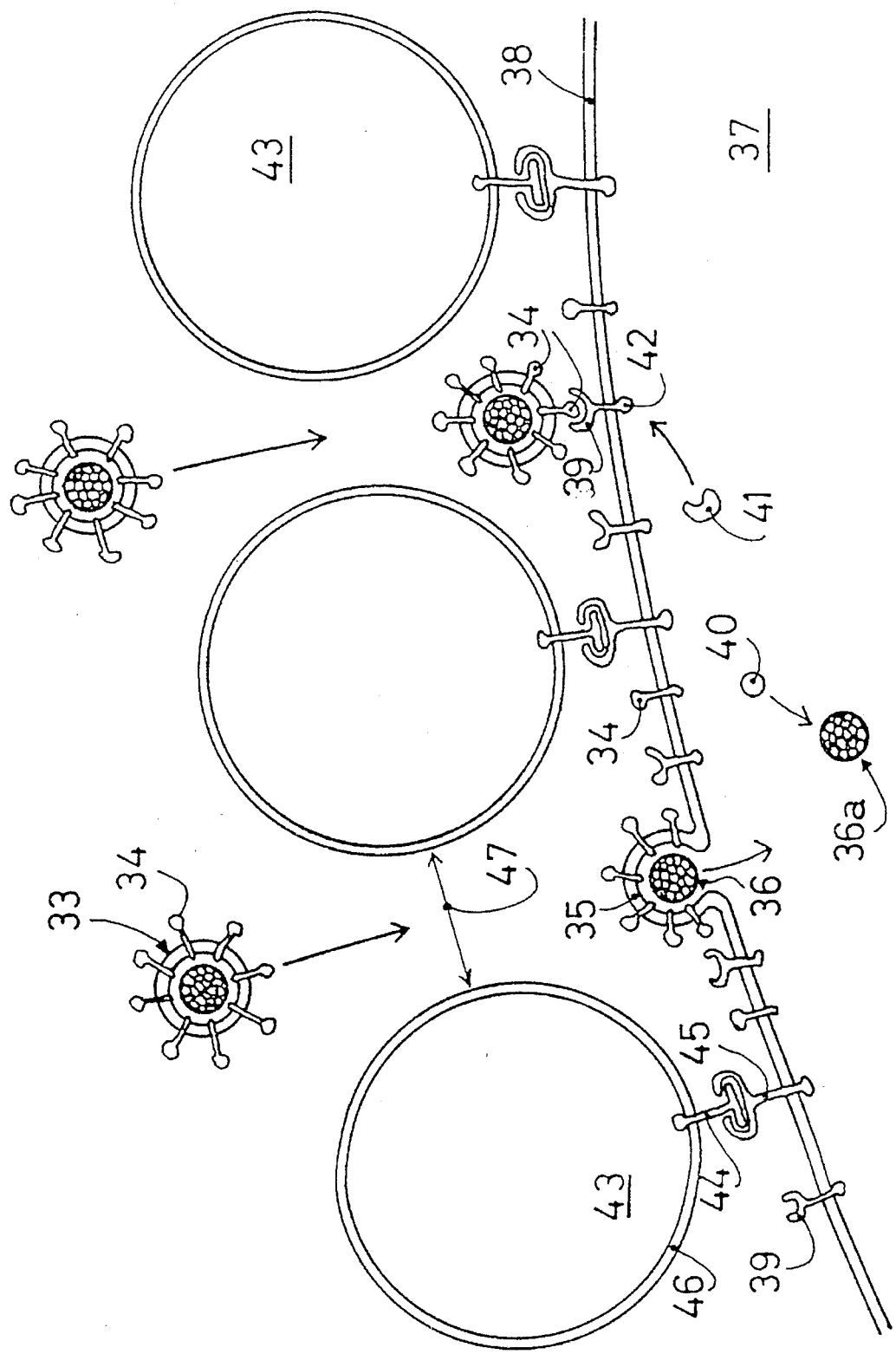
FIG. 7 shows a CD4 carrying liposome coated by a number of smaller liposomes in order to reduce antigenicity of the complex—the size of HIV particeles allows for their access to and interaction with CD4.

FIG. 7 shows a portion of the large liposome 37, coated by a number of small liposomes 43 in order to render the outside of the complex non-antigenic. Viral particles 33 with their envelope proteins 34 (gp120) can fit through spaces 47 between small liposomes 43 (these are shown here in a cross-section—viewed in the direction perpendicular to the surface of the large liposome 37, small liposomes, packed as spheres, leave triangular openings which should be large enough to allow passage of the virus, see FIG. 9). As described earlier, through interaction of the viral envelope protein 34 (gp120) and the receptor 39 (CD4), followed by action of protein kinase C, 41, on the anchor of CD4, the membranes 35 of the virus and 38 of the large liposome fuse and the core 36 of the virus enters the liposome 37. Core proteins 36a of the virus core can be cleaved by enzyme 40. Small liposomes 43 are anchored to the large liposome 37 by a pair of link molecules—44 which is anchored in the membrane 46 of the small liposomes, and 45 which is anchored in the membrane 38 of the large liposome. There should be at most one such molecule 44 per one small liposome. The number of link molecules 45 on the large liposome is to be calculated so that most of its surface ends up covered by small ones. An example of this calculation is given in connection with FIG. 9. Note that a large liposome—small liposome complex shown here is of potential benefit even if the fusion and viral core internalization do not occur. Collecting viral particles on the receptors 39 (CD4) does remove them from circulation and interaction with the natural CD4-carrying targets. This, however will not lead to destruction of the viral particles, and in an eventual attack by the immune system on the complexes, virus could infect the attacking cells (macrophages).

Figure 8:
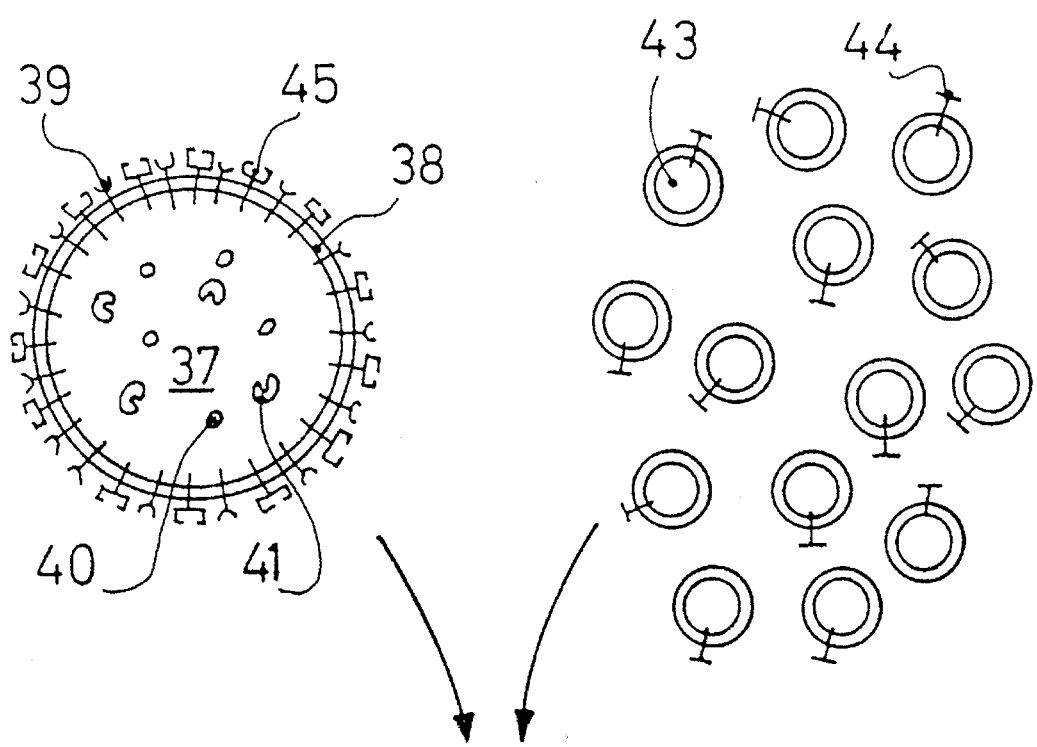
FIG. 8 shows the process of preparation of the large/small liposome complex.
Figure 8:
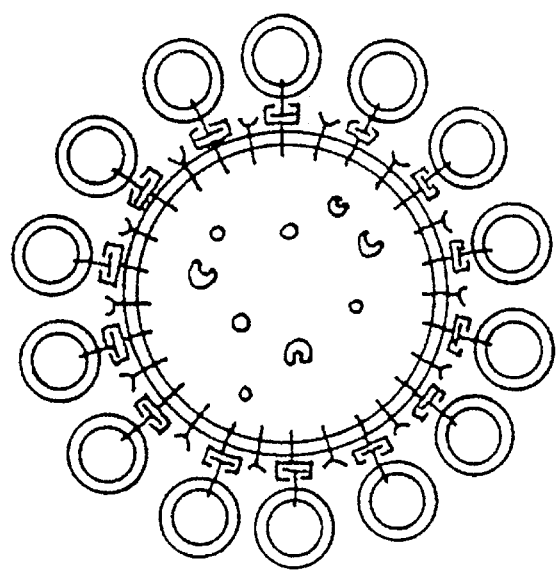

FIG. 8 shows the preparation procedure of the complexed liposomes. On one side, large liposomes are prepared with the receptors 39 (CD4) and link molecules 45 anchored in the membrane 38. Enzymes 40 and 41 are enclosed in the interior of the liposome 37. On the other side, small liposomes 43 are prepared with a link molecule 44 anchored in the membrane—there should be no more than one such molecule per liposome. When the two preparations are brought together, the pair 44/45 interacts and binds the small liposomes to large ones. Many such link molecules are known in the art. The distance (determined by the combined length of the molecules) between the liposomes should be large enough to prevent fusion of the two bilayers. One example is biotin/streptavidin. Biotinized phospholipids are commercially available and can be used (mixed in appropriate concentration with normal phospholipids) to prepare one side of the link. Streptavidin can be anchored in the bilayer of the other side by any number of techniques, including light-induced coupling described by M. SANGER, et al. in "Light-Induced Coupling of Aqueous-Soluble Proteins to Liposomes Formed from Carbene-Generating Phospholipids", Bioconjugate Chemistry, Vol. 3, No. 4, 1992.

Figure 9A:
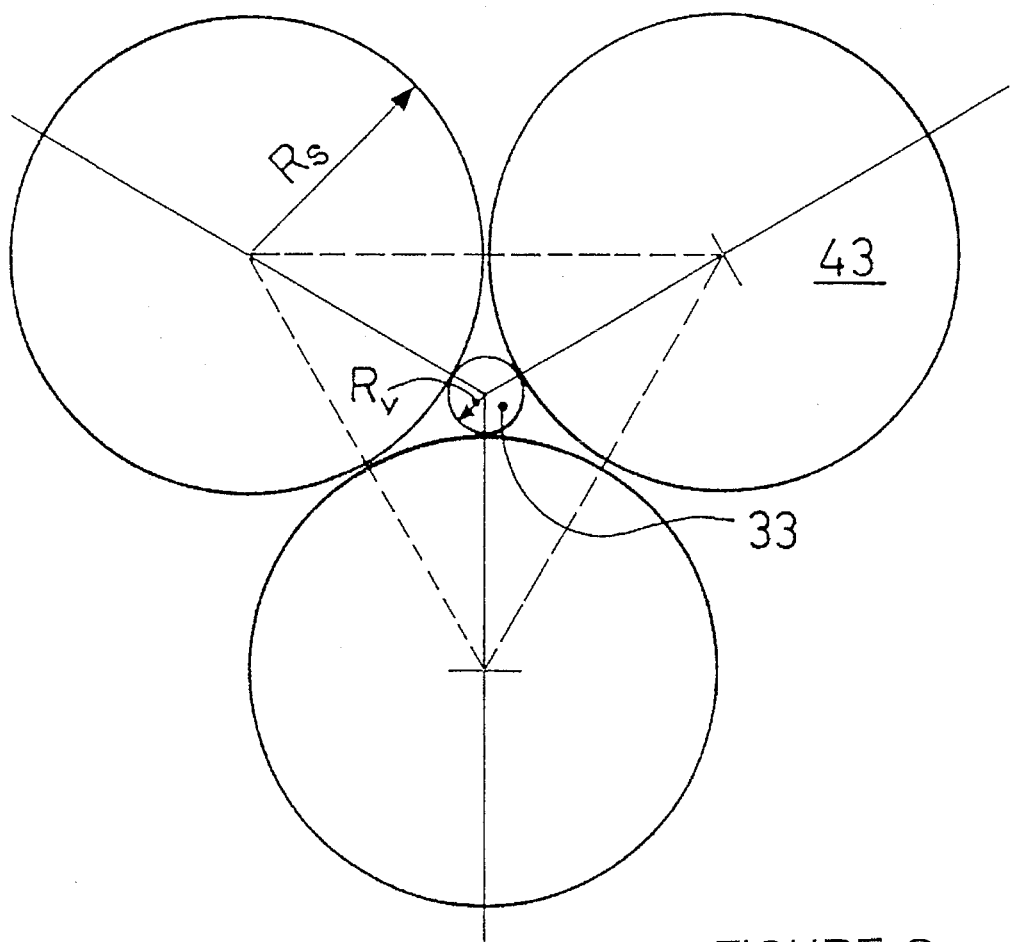
FIG. 9a shows geometrical relations between the virus and the smaller liposomes.
Figure 9B:
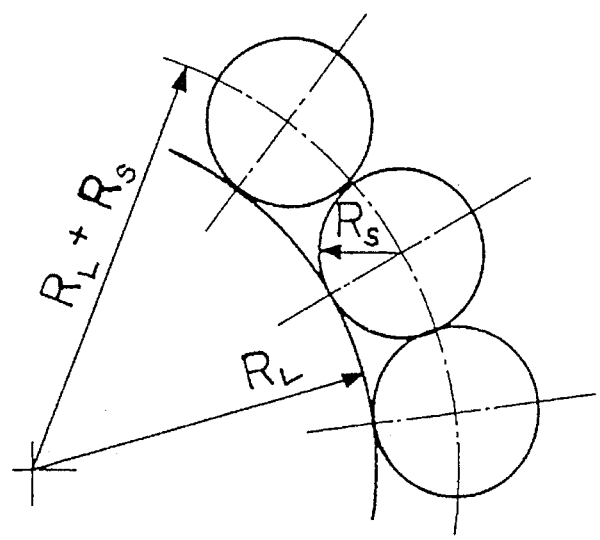
FIG. 9b shows geometrical relations between the large and small liposomes.

FIGS. 9a and 9b show an example of calculations for size and number of small liposomes. With respect to FIG. 9a, let $R_V$ be the radius of the virus (0.05 microns), $R_S$ radius of the smaller liposomes and $R_L$ radius of the large liposome. If the small liposomes are (semi) tightly packed around the large one and only the spaces between them will be open for virus entry, we can write from simple geometrical relations:

$$(R_V+R_S)=2/3\times 2R_S\times 1.73/2,$$

which gives $R_S=6R_V$ (approx.). Thus, since $R_V=0.05$ microns, we can choose $R_S=0.3$ microns.

FIG. 9b shows the geometrical relationship between the small liposomes and the large one. The spherical surface on which the centers of small liposomes reside has the radius $(R_L+R_S)$. The area of this surface is:

$$A_S=4(R_L+R_S)^2\times 3.14.$$

If we choose $R_L=2$ microns, $A_S=66$ microns$^2$. Cross-section of the small liposomes at equator is $A_O=0.3$ microns$^2$ and efficiency of packing is about 90%. This leads to the number of small liposomes:

$$N=0.9\times 66/0.3=200 \text{ (approx.).}$$

This was with the selected $R_L=2$ microns, and $R_S=0.3$ microns, calculated from $R_V=0.05$ microns. Should we choose $R_L=1$ microns, the number of small liposomes will be N=65 (approx.).

As mentioned above, the number of link molecules incorporated into large liposomes should correspond approximately to these calculations in order to get dense covering of the large liposome by small ones. Small liposomes are subject to random movements confined by their anchorage to the large one—size of the openings will fluctuate, but with the approach presented, there should always be enough room for the virus to pass through and reach the receptors in the membrane of the large liposome.

I claim:

1. A therapeutic composition of matter for use against viruses possessing an outer lipid envelope and an inner viral core, wherein said therapeutic composition is in the form of a liposome complex with a non-antigenic exterior, said therapeutic composition comprising:

a large liposome with an outer membrane and an aqueous fluid-filled interior;

a plurality of viral receptor proteins capable of reacting with the outer lipid envelope of the virus, wherein said viral receptor proteins are incorporated in said large lipid membrane;

a plurality of small liposomes, each with an outer membrane and an aqueous fluid-filled interior, wherein said outer membrane is substantially free of antigens except for a single first link protein; and a plurality of second link proteins incorporated in said large lipid membrane, wherein each first link protein in a small lipid membrane is linked to a second link protein in the large lipid membrane so that most of the surface of the large lipid membrane is covered by the small lipid membranes leaving gaps large enough for the virus to pass between the small liposomes;

wherein said therapeutic composition is capable of engulfing said viruses by allowing the viruses to travel between the small liposomes and to for the viral lipid envelope to interact with the viral receptor protein and fuse with the large liposome membrane so that the core of the virus is trapped in the interior of the large liposome.

2. A composition according to claim 1, wherein the viral receptor protein in the large liposome membrane is a CD4 protein or a CD4 protein fragment capable of interaction with the human immunodeficiency virus (HIV).

3. A composition according to claim 1, wherein said large liposome interior fluid filled vesicle further comprises a protein kinase C enzyme, so that said enzyme is encapsulated by said large liposome membrane.

4. A composition according to claim 1, wherein said large liposome interior fluid filled vesicle further comprises an anti-viral agent in the form of an enzyme capable of cleaving the viral core proteins, so that the anti-viral agent is encapsulated by the large liposome membrane.

5. A composition according to claim 1, wherein said large liposome interior fluid filled vesicle further comprises magnetic particles encapsulated within the large liposome membrane, wherein said magnetic particles are capable of disrupting the liposome complex in a rotating magnetic field to disperse the engulfed viral cores.

6. The therapeutic composition of claim 1 wherein said large liposome is a large unilamellar vesicle (LUV) with a diameter in the range of about one micron to about 10 microns.

7. The therapeutic composition of claim 1 wherein one of said link proteins is streptavidin.

* * * * *